United States Patent
Zhang et al.

(10) Patent No.: US 7,223,288 B2
(45) Date of Patent: May 29, 2007

(54) ACCOMMODATIVE INTRAOCULAR LENS

(75) Inventors: Xiaoxiao Zhang, Fort Worth, TX (US); Yin Yang, Arlington, TX (US)

(73) Assignee: Alcon, Inc., Hunenburg (CH)

(*) Notice: Subject to any disclaimer, the term of this patent is extended or adjusted under 35 U.S.C. 154(b) by 527 days.

(21) Appl. No.: 10/787,863

(22) Filed: Feb. 26, 2004

(65) Prior Publication Data
US 2004/0236422 A1    Nov. 25, 2004

Related U.S. Application Data

(63) Continuation-in-part of application No. 10/442,771, filed on May 21, 2003, now Pat. No. 7,029,497.

(51) Int. Cl.
*A61F 2/16*    (2006.01)

(52) U.S. Cl. .................. 623/6.34; 623/6.37; 623/6.44; 623/6.47

(58) Field of Classification Search ............... 623/6.34, 623/6.37, 6.44, 6.47, 6.49, 6.51, 6.11, 6.22, 623/6.32, 6.38, 6.43
See application file for complete search history.

(56) References Cited

U.S. PATENT DOCUMENTS

| | | | |
|---|---|---|---|
| 4,892,543 A * | 1/1990 | Turley | ........................ 623/6.13 |
| 5,275,623 A | 1/1994 | Sarfarazi | |
| 5,476,514 A | 12/1995 | Cumming | |
| 5,496,366 A | 3/1996 | Cumming | |
| 5,674,282 A | 10/1997 | Cumming | |
| 6,197,059 B1 | 3/2001 | Cumming | |
| 6,241,777 B1 | 6/2001 | Kellan | |
| 6,261,321 B1 | 7/2001 | Hanna | |
| 6,302,911 B1 | 10/2001 | Hanna | |
| 6,616,691 B1 * | 9/2003 | Tran | ........................ 623/6.11 |

(Continued)

FOREIGN PATENT DOCUMENTS

WO    WO 01/34067    11/1999

(Continued)

OTHER PUBLICATIONS

"A dual optic accommodating foldable intraocular lens" British Journal of Ophthalmology 2003;87:1083-1085.

*Primary Examiner*—David H. Willse
(74) *Attorney, Agent, or Firm*—Jeffrey S. Schira

(57) ABSTRACT

A two-optic accommodative lens system. The first lens has a negative power and is located posteriorly within the capsular bag and laying against the posterior capsule. The periphery of the first lens contains a pair of generally T-shaped haptics oriented along a vertical meridian of the capsular bag and having a generally rectangular slot within the top portion of the "T". The first lens further having a plurality of elongated haptics oriented along a horizontal meridian of the capsular bag. The second lens is located anteriorly to the first lens outside of the capsular bag and is of a positive power. The peripheral edge of the second lens contains a pair of encircling haptics having a notched tab sized and shape to fit within the slots in the haptics on the first lens to lock the second lens onto the first lens. Hinge structures on the encircling haptics allow the second lens to move relative to the first lens along the optical axis of the lens system in reaction to movement of the ciliary muscle.

5 Claims, 4 Drawing Sheets

U.S. PATENT DOCUMENTS

| | | |
|---|---|---|
| 6,818,158 B2 | 11/2004 | Pham et al. |
| 2002/0107568 A1 | 8/2002 | Zadno-Azizi et al. |
| 2004/0039446 A1 | 2/2004 | McNicholas |
| 2004/0111151 A1 | 6/2004 | Paul et al. |
| 2004/0127984 A1 | 7/2004 | Paul et al. |

FOREIGN PATENT DOCUMENTS

| | | |
|---|---|---|
| WO | WO 00/66037 | 11/2000 |
| WO | WO 03/059196 | 7/2003 |
| WO | WO 03/059208 | 7/2003 |

\* cited by examiner

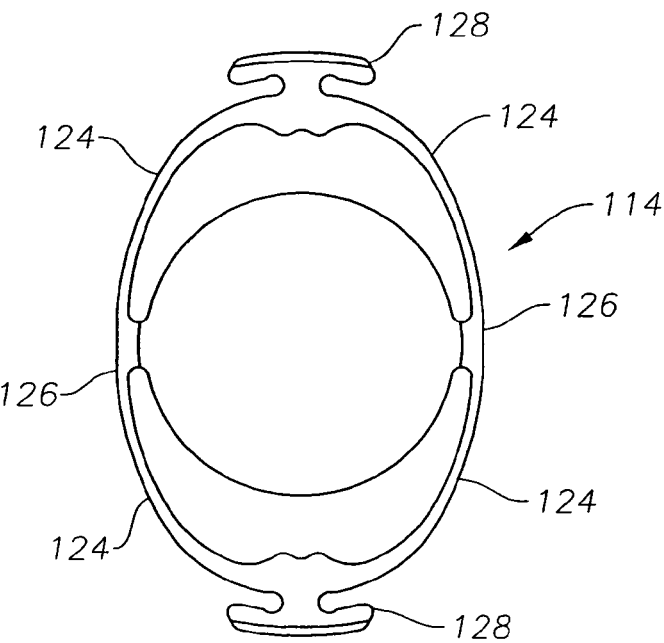
Fig. 3
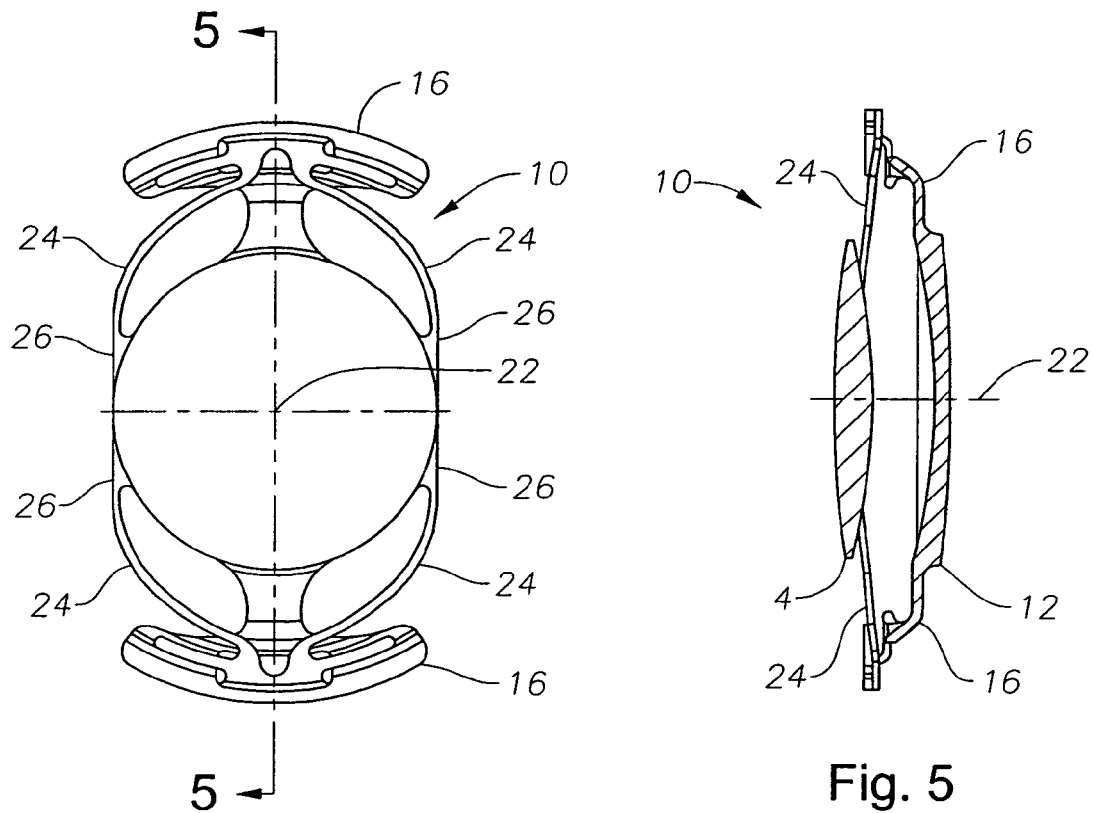
Fig. 4
Fig. 5

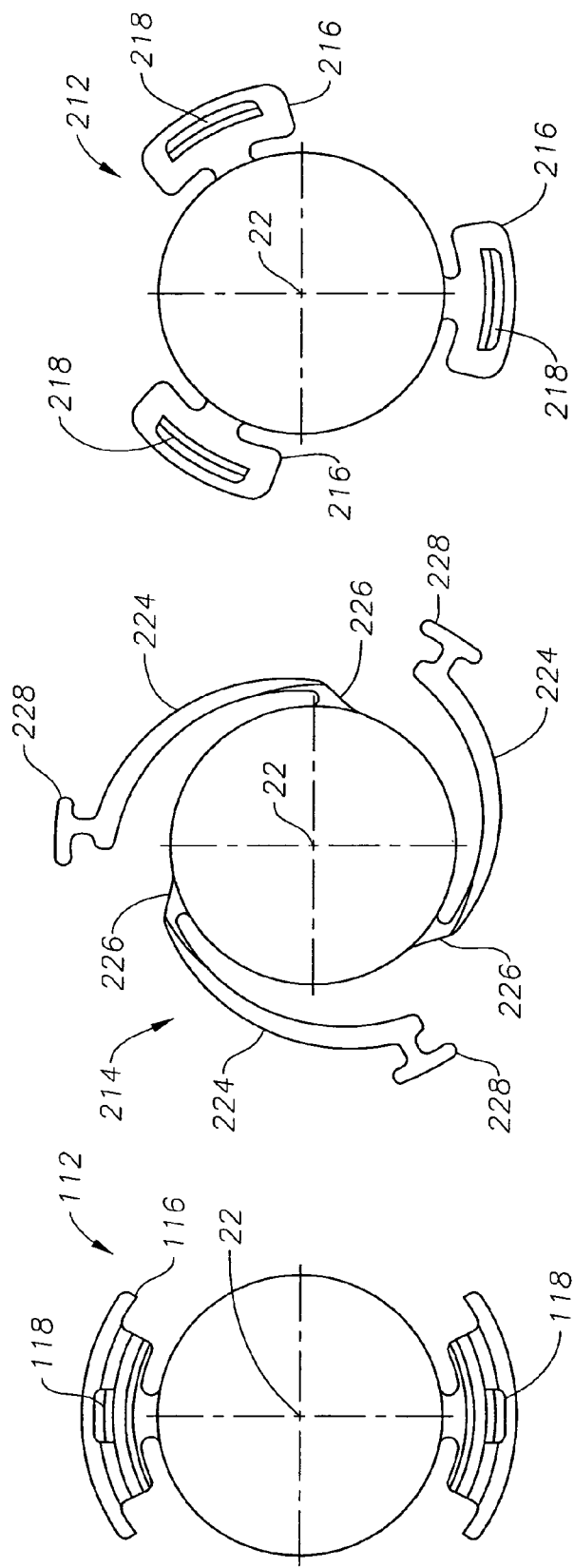

ACCOMMODATIVE INTRAOCULAR LENS

This application is a continuation-in-part of U.S. patent application Ser. No. 10/442,771, filed May 21, 2003, now U.S. Pat. No. 7,029,497.

BACKGROUND OF THE INVENTION

This invention relates generally to the field of intraocular lenses (IOL) and, more particularly, to accommodative IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In that way, the natural lens can be focused alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Prior to the present invention, when a cataract or other disease required the removal of the natural lens and replacement with an artificial IOL, the IOL was a monofocal lens, requiring that the patient use a pair of spectacles or contact lenses for near vision. Advanced Medical Optics has been selling a bifocal IOL, the Array lens, for several years, but due to quality issues, this lens has not been widely accepted.

Several designs for accommodative IOLs are being studied. For example, several designs manufactured by C&C Vision are currently undergoing clinical trials. See U.S. Pat. Nos. 6,197,059, 5,674,282, 5,496,366 and 5,476,514 (Cumming), the entire contents of which being incorporated herein by reference. The lens described in these patents is a single optic lens having flexible haptics that allows the optic to move forward and backward in reaction to movement of the ciliary muscle. A Similar designs are described in U.S. Pat. No. 6,302,911 B1 (Hanna), U.S. Pat. Nos. 6,261,321 B1 and 6,241,777 B1 (both to Kellan), the entire contents of which being incorporated herein by reference. The amount of movement of the optic in these single-lens systems, however, may be insufficient to allow for a useful range of accommodation. In addition, as described in U.S. Pat. Nos. 6,197,059, 5,674,282, 5,496,366 and 5,476,514, the eye must be paralyzed for one to two weeks in order for capsular fibrosis to entrap the lens to thereby provide for a rigid association between the lens and the capsular bag. In addition, the commercial models of these lenses are made from a hydrogel or silicone material. Such materials are not inherently resistive to the formation of posterior capsule opacification ("PCO"). The only treatment for PCO is a capsulotomy using a Nd:YAG laser that vaporizes a portion of the posterior capsule. Such destruction of the posterior capsule may destroy the mechanism of accommodation of these lenses.

There have been some attempts to make a two-optic accommodative lens system. For example, U.S. Pat. No. 5,275,623 (Sarfarazi), WIPO Publication No. 00/66037 (Glick, et al.) and WO 01/34067 A1 (Bandhauer, et al), the entire contents of which being incorporated herein by reference, all disclose a two-optic lens system with one optic having a positive power and the other optic having a negative power. The optics are connected by a hinge mechanism that reacts to movement of the ciliary muscle to move the optics closer together or further apart, thereby providing accommodation. In order to provide this "zoom lens" effect, movement of the ciliary muscle must be adequately transmitted to the lens system through the capsular bag, and none of these references disclose a mechanism for ensuring that there is a tight connection between the capsular bag and the lens system. In addition, none of these lens designs have addressed the problem with PCO noted above.

Therefore, a need continues to exist for a safe and stable accommodative intraocular lens system that provides accommodation over a broad and useful range.

BRIEF SUMMARY OF THE INVENTION

The present invention improves upon the prior art by providing a two-optic accommodative lens system. The first lens has a negative power and is located posteriorly within the capsular bag and laying against the posterior capsule. The periphery of the first lens contains a pair of generally T-shaped haptics oriented along a vertical meridian of the capsular bag and having a generally rectangular slot within the top portion of the "T". The first lens further has a plurality of elongated haptics oriented along a horizontal meridian of the capsular bag. The second lens is located anteriorly to the first lens outside of the capsular bag and is of a positive power. The peripheral edge of the second lens contains a pair of encircling haptics having a notched tab sized and shaped to fit within the slots in the haptics on the first lens to lock the second lens onto the first lens. Hinge structures on the encircling haptics allow the second lens to move relative to the first lens along the optical axis of the lens system in reaction to movement of the ciliary muscle.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible accommodative lens system.

BRIEF DESCRIPTION OF THE DRAWINGS

FIG. 3 is an enlarged top plan view of the second embodiment of the second lens of the lens system of the present invention.

FIG. 4 is an enlarged top plan view of the first embodiment of the first lens connected to the first embodiment of the second lens of the lens system of the present invention.

FIG. 5 is an enlarged cross-sectional view of the first embodiment of the first lens connected to the first embodiment of the second lens of the lens system of the present invention taken at line 5-5 in FIG. 4.

FIG. 6 is an enlarged top plan view of the second embodiment of the first lens of the lens system of the present invention.

FIG. 7 is an enlarged top plan view of the third embodiment of the second lens of the lens system of the present invention.

FIG. 8 is an enlarged top plan view of the third embodiment of the first lens of the lens system of the present invention.

DETAILED DESCRIPTION OF THE INVENTION

Figure 1:
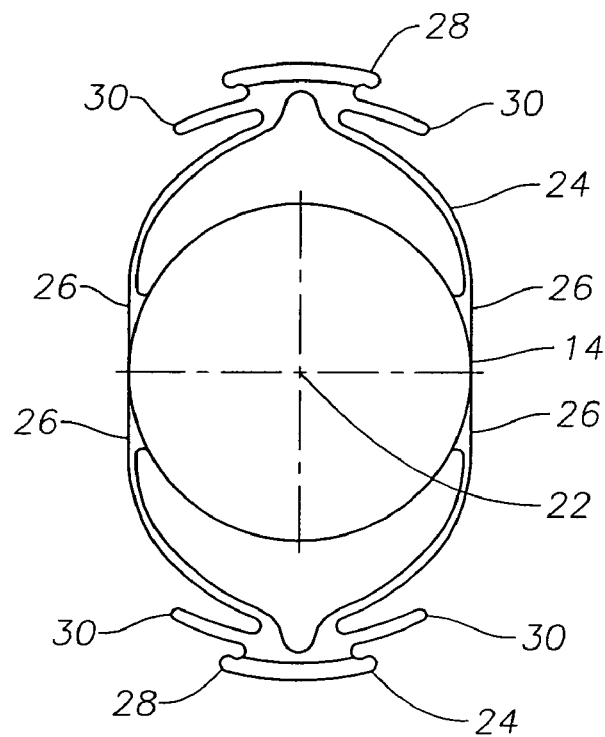
FIG. 1 is an enlarged top plan view of the first embodiment of the second lens of the lens system of the present invention.

As best seen in FIGS. 1, 2, 4 and 5, lens system 10 of the present invention generally consists of posterior optic 12 and anterior optic 14. Optic 12 is preferably formed in any suitable overall diameter or length, for example, around 10 millimeters, for implantation in the posterior chamber. Optic 12 preferably is made from a soft, foldable material that is inherently resistive to the formation of PCO, such as a soft acrylic. Optic 14 preferably is made from a soft, foldable material such as a hydrogel, silicone or soft acrylic. Optic 12 may be any suitable power, but preferably has a negative power. Optic 14 may also be any suitable power but preferably has a positive power. The relative powers of optics 12 and 14 should be such that the axial movement of optic 14 toward or away from optic 12 should be sufficient to adjust the overall power of lens system 10 at least one diopter and preferably, at least three to four diopters, calculation of such powers of optics 12 and 14 being within the capabilities of one skilled in the art of designing ophthalmic lenses by, for example, using the following equations:

$$P = P_1 P_2 - T/n * P_1 P_2 \quad (1)$$

$$\delta P = \delta T/n * P_1 P_2 \quad (2)$$

Wherein
P is the power of the lens system;
$P_1$ is the power of the 1st lens in the lens system;
$P_2$ is the power of the 2nd lens in the lens system;
T is the separation between the 1st and the 2nd lenses;
n is the refractive index of the medium between the 1st and the 2nd lenses;
$\delta P$ is the change of P;
$\delta T$ is the change of T.

Figure 2:
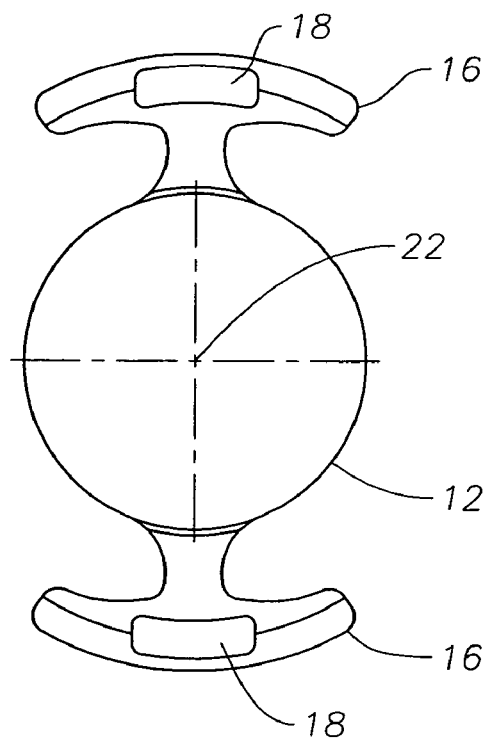
FIG. 2 is an enlarged top plan view of the first embodiment of the first lens of the lens system of the present invention.

As best seen in FIGS. 1 and 2, optic 12 is generally symmetrical about optical axis 22 and contains opposing, generally T-shaped haptics 16 that are shaped to stretch and fill the equatorial region of the capsular bag. Haptics 16 contain slots 18 that penetrate all the way through haptics 16. As best seen in FIG. 1, optic 14 contains a pair of haptics 24 that are connected to optic 14 by hinge regions 26 and contain notched tabs 28 carried at the distal ends of haptics 24. As seen in FIGS. 4 and 5, tabs 28 are sized and shaped to penetrate and fit within slots 18 on optic 12, thereby holding optic 14 firmly within optic 12 while still permitting rotation of locking tabs 28 within slots 18. One skilled in the art will recognize that slots 18 may be located on haptics 24 and that tabs 28 may be located on optic 12. In order to remove the natural lens, an opening or rhexis is normally made in the anterior side of the capsular bag. The opening contains rim or margin. During implantation of system 10, the rim or margin is inserted into slot 18 prior to the introduction of optic 14. Once optic 14 is installed in optic 12, tabs 28 help to contain the rim within slots 18, thereby maintaining a positive mechanical connection between the capsular bag and lens system 10. In addition, fingers 30 on haptics 24 remain on the anterior of slots 18, as seen in FIG. 4, and help to hold the rim tightly against haptics 16. Contraction of the capsular bag will therefore be more directly translated into contraction of optic 12, with resulting vaulting of optic 14 away from optic 12 about hinge regions 26. One skilled in the art will recognize that no specific feature needs to be used to form hinge regions 26 as haptics 24 may be formed from a material and/or in such a configuration that haptics naturally flex in the manner of a hinge.

Alternatively, optic 14 may be of slightly larger diameter of optic 12 so that haptics 24 must be compressed about hinge regions 26 in order for tabs 28 to fit within slots 18. Such compression of haptics 24 causes optic 14 to elongate along optical axis 22. Therefore, when optic 14 is connected to optic 12, optic 14 will be spaced apart from optic 12. In such circumstances, relaxation of the ciliary muscle will cause optic 12 to stretch, thereby reducing the compression of optic 14, allowing optic 14 to move closer to optic 12 along optical axis 22.

As best seen in FIG. 3, in a second embodiment, anterior optic 114 is of similar construction as optic 14, having haptics 124 that are connected to optic 114 by hinge regions 126 and containing notched tabs 128 carried at the distal ends of haptics 124. Tabs 128 are sized and shaped to fit within slots 18 on optic 12, thereby holding optic 114 firmly within optic 12 while still permitting rotation of locking tabs 128 within slots 18.

As best seen in FIG. 6, in a second embodiment, posterior optic 112 is of similar construction as optic 12, being generally symmetrical about optical axis 22 and containing opposing, generally T-shaped haptics 116 that are shaped to stretch and fill the equatorial region of the capsular bag. Haptics 116 contain slots 118.

As best seen in FIG. 8, in a third embodiment of the present invention, optic 212 is generally symmetrical about optical axis 22 and contains opposing, generally T-shaped haptics 216 that are shaped to stretch and fill the equatorial region of the capsular bag. Haptics 216 contain slots 218 that penetrate all the way through haptics 216. As best seen in FIG. 7, optic 214 contains a plurality of haptics 224 that are connected to optic 214 by hinge regions 226 and contain notched tabs 228 carried at the distal ends of haptics 224. Tabs 228 are sized and shaped to fit within slots 218 on optic 212, thereby holding optic 214 firmly within optic 212 while still permitting rotation of locking tabs 228 within slots 218. One skilled in the art will recognize that slots 218 may be located on haptics 224 and that tabs 228 may be located on optic 212.

Figure 10:
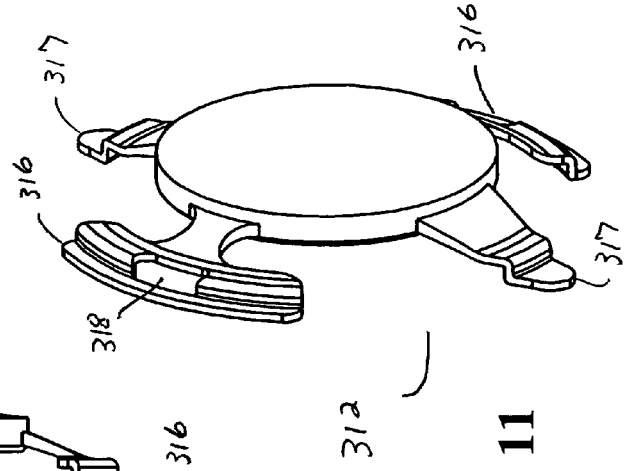
FIG. 10 is an enlarged cross-sectional view of a fourth embodiment of the first lens of the lens system of the present invention.
Figure 11:
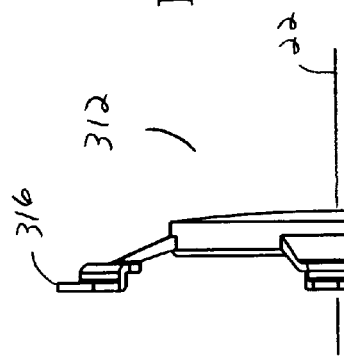
FIG. 11 is an enlarged perspective view of a fourth embodiment of the first lens of the lens system of the present invention.
Figure 9:
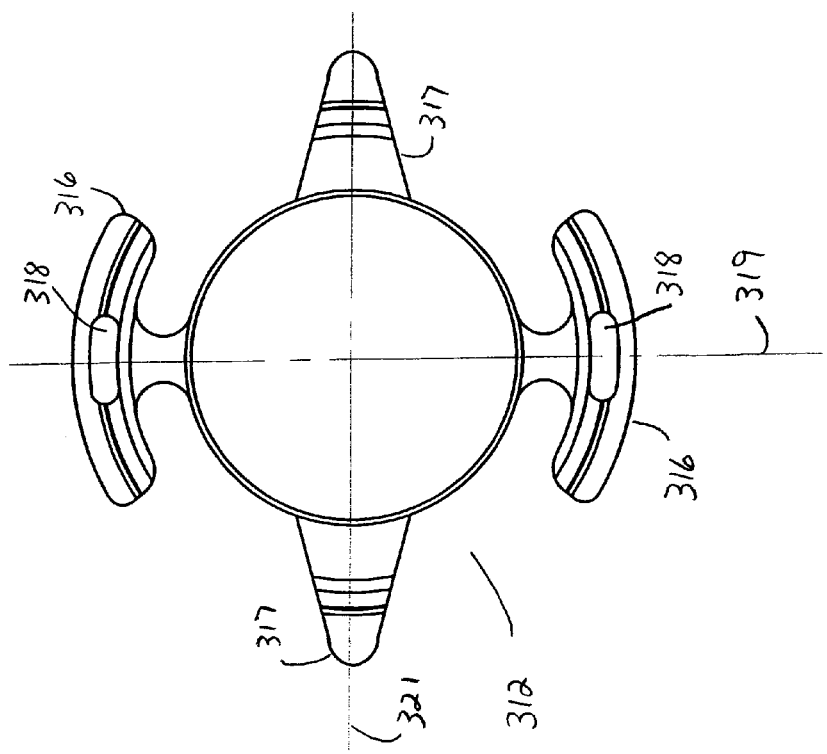
FIG. 9 is an enlarged top plan view of a fourth embodiment of the first lens of the lens system of the present invention.

As best seen in FIGS. 9, 10 and 11, optic 312 is generally symmetrical about optical axis 22 and contains opposing, generally T-shaped haptics 316 that are oriental along vertical meridian 319 of the capsule bag and are shaped to fill the equatorial region of the capsular bag. Hap tics 316 contain slots 318 that penetrate all the way through haptics 316. Optic 312 also contains elongated horizontal meridian haptics 317. When optic 312 is implanted, horizontal meridian haptics 317 are implanted so that horizonal meridian 312 of the capsular bag is stretched outward by length of haptics 317, thereby relaxing the zonules and causing the capsular bag to assume a slightly oval shape. This "ovaling" of the capsular bag along the horizontal meridian is limited by tension in the zonules along the vertical meridian, which do not allow the capsular bag along the vertical meridian to constrict narrower than the normal diameter of the capsular bag. This constriction limitation prevents forward movement of optics 14 or 114 along the visual axis. During accommodation, the zonules located along the vertical meridian of the capsule bag relax, allowing the capsule bag to constrict haptics 24 or 124 along the vertical meridian while the length of optic 312 along the length of haptics 317 remains relatively unchanged, resulting in a more pronounced ovaling of the capsular bag. This constriction of haptics 24 or 124 along the vertical meridian is transferred to optics 14 or 114, respectively, through hinge regions 26 or 126, pushing optics 14 or 114 anteriorly along visual axis 22.

This description is given for purposes of illustration and explanation. It will be apparent to those skilled in the relevant art that changes and modifications may be made to the invention described above without departing from its scope or spirit.

We claim:

1. An intraocular lens, comprising:
   a) a first lens having a plurality of generally T-shaped haptics oriented along a vertical meridian and a plurality of elongated haptics oriented along a horizontal meridian, wherein the haptics oriented along the horizontal meridian are longer than the haptics oriented along the vertical meridian and the haptics oriented along the horizontal meridian stretch a capsular bag outward when the first lens is implanted in the capsular bag and wherein the haptics oriented along the vertical meridian contain a slot, the slots penetrating through the haptics;
   b) a second lens;
   c) at least one haptic associated with the second lens, the haptic being connected to the second lens by a hinge region; and
   d) a notched tab located on the haptic of the second lens, the notched tab sized and shaped to be received in the slot, penetrating through the slot and thereby movably attach the second lens to the first lens.

2. The lens of claim 1 wherein the hinge region allows the second lens to vault away from the first lens in reaction to compression of the first lens.

3. The lens of claim 1 wherein the first lens and the second lens comprise a soft acrylic material.

4. The lens of claim 1 wherein the second lens comprises a hydrogel material.

5. The lens of claim 1 wherein the second lens comprises a silicone material.

* * * * *